United States Patent [19]
Whitehead

[11] Patent Number: 5,679,793
[45] Date of Patent: Oct. 21, 1997

[54] PROCESS FOR THE PREPARATION OF SUBSTITUTED PYRAZINES

[75] Inventor: Ian Michael Whitehead, Geneva, Switzerland

[73] Assignee: Firmenich SA, Geneva, Switzerland

[21] Appl. No.: 569,173

[22] PCT Filed: Mar. 28, 1995

[86] PCT No.: PCT/IB95/00212

§ 371 Date: Dec. 15, 1995

§ 102(e) Date: Dec. 15, 1995

[87] PCT Pub. No.: WO95/30660

PCT Pub. Date: Nov. 16, 1995

[30] Foreign Application Priority Data

May 10, 1994 [CH] Switzerland ............... 1448/94

[51] Int. Cl.⁶ ............... C07D 241/12; C07D 241/38
[52] U.S. Cl. ............... 544/349; 544/336; 544/354; 544/410
[58] Field of Search ............... 544/336, 410, 544/349, 353

[56] References Cited

U.S. PATENT DOCUMENTS 3,544,682  12/1970  Taylor et al. ............... 544/336
3,928,352  12/1975  Taylor ............... 544/336

FOREIGN PATENT DOCUMENTS 505891  9/1992  European Pat. Off. .

OTHER PUBLICATIONS

Chemical Abstracts, vol. 88, No. 15, 1978, Abstract No. 88: 105411e, p. 582; column 2.
Rizzi, George P., "Formation of Pyrazines from Acyloin Precursors under Mild Conditions", J. Agric. Food Chem. 11988, 36, pp. 349–352.

*Primary Examiner*—Emily Bernhardt
*Attorney, Agent, or Firm*—Pennie & Edmonds

[57] ABSTRACT

Process for the preparation of substituted pyrazines comprising the reaction of a dihydroxyketone of formula

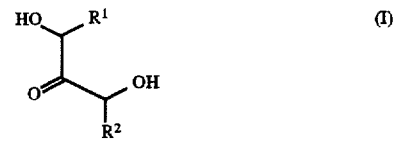

(I)

wherein $R^1$ et $R^2$ each represent a hydrogen atom, a saturated or unsaturated, linear or branched, hydrocarbon radical having 1 to 6 carbon atoms, or a —$CH_2OH$ group, with an ammonium salt, or, as the case may be, with an ammonium salt and an acyloin of formula

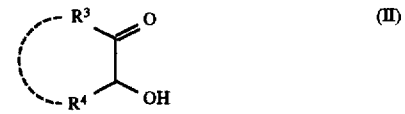

(II)

wherein $R^3$ and $R^4$ have the meaning indicated in formula (IV).

The process is particularly useful for preparing asymmetrical alkylpyrazines.

10 Claims, No Drawings

PROCESS FOR THE PREPARATION OF SUBSTITUTED PYRAZINES

This application is a 371 of PCT/IB95/00212 filed Mar. 28, 1995.

TECHNICAL FIELD

The present invention relates to the field of organic synthesis and, more particularly, to that of the preparation of substituted pyrazines.

The substituted pyrazines, and in particular alkylpyrazines, are very important flavoring ingredients, mostly of natural origin. Namely, they are present in a great many fermented products or in products which undergo a thermal treatment.

On the other hand, these alkylpyrazines are also useful as starting products for the preparation of other pyrazine derivatives and thus play an important role in organic synthesis.

PRIOR ART

Processes for the preparation of alkylpyrazines are already known, which are particularly adapted to the synthesis of natural products. For example, G. P. Rizzi, in J. Agr. Food Chem 36, 349 (1988), describes a process for the preparation of alkylpyrazines via the reaction of acyloins with ammonium acetate, under so-called "soft" reaction conditions. This process requires a complex procedure, with a long reaction time.

On the other hand, in European patent application n° 505 891, there is disclosed a process which makes use of the same reaction, but wherein the latter is carried out at reflux in water, if need be with simultaneous sublimation of the reaction mixture.

These two processes enable the preparation of symmetrical alkylpyrazines, but do not provide a satisfactory solution to the problem of the preparation of asymmetrical substituted pyrazines, which preparation is known to be far more difficult.

DESCRIPTION OF THE INVENTION

The aim of the present invention is precisely to provide a novel solution to this problem, by realizing a process of very general application which makes it possible to obtain substituted pyrazines, of natural or synthetic origin, and in particular asymmetrical alkylpyrazines. Thus, the invention relates to a process for the preparation of a pyrazine of formula

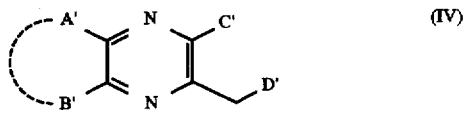

wherein $A=B=C=D=R^1=R^2$, or wherein $A=C=R^1$, $B=D=R^2$, and $R^1 \neq R^2$, or $A=D=R^1$, $B=C=R^2$ and $R^1 \neq R^2$, symbols $R^1$ and $R^2$ representing each a hydrogen atom, a saturated or unsaturated, linear or branched, hydrocarbon radical having 1 to 6 carbon atoms or a —$CH_2OH$ group; or respectively of formula

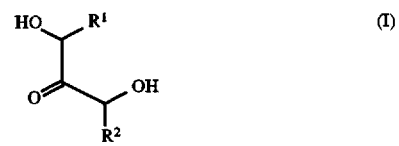

wherein $A'=R^3$, $B'=R^4$ or vice versa and $C'=R^1$, $D'=R^2$, $R^1$ and $R^2$ being identical or different and having the above-mentioned meaning and $R^3$ and $R^4$ being identical or different and representing each a $C_1$ to $C_6$, saturated or unsaturated, hydrocarbon radical, or a saturated or unsaturated cyclic radical, substituted or unsubstituted, having 5 or 6 carbon atoms in the ring, or being identical and representing a CH or $CH_2$ group belonging to a ring such as indicated by the dotted line, containing 5 or 6 carbon atoms, substituted or unsubstituted, the process being characterized by the reaction, in an inert organic solvent, of a compound of formula

wherein $R^1$ and $R^2$ are identical or different and have the meaning indicated above, with an ammonium salt, or respectively with an ammonium salt and an acyloin of formula

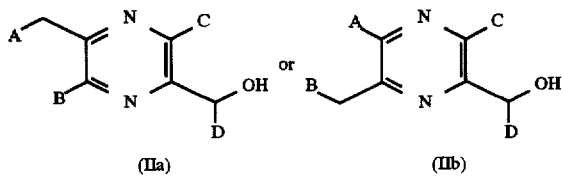

wherein $R^3$ and $R^4$ have the meaning indicated in formula (IV) and, if need be, by the separation of said pyrazine from the reaction product.

The process of the invention is based on the principle of the use of formula (I) dihydroxyketone as a substrate which reacts with the ammonium salt. Without wanting to prejudge on the mechanism of the reaction, it is possible that this dihydroxyketone self-reacts or reacts with the acyloin of formula (III) to form the (di)-hydroxymethyl-dihydropyrazines, the latter undergoing spontaneous dehydration to yield the desired substituted pyrazines. Thus, in the particular case of 1,3-dihydroxy-2-propanone, its self-reaction yields the hydroxypyrazine represented in the following scheme:

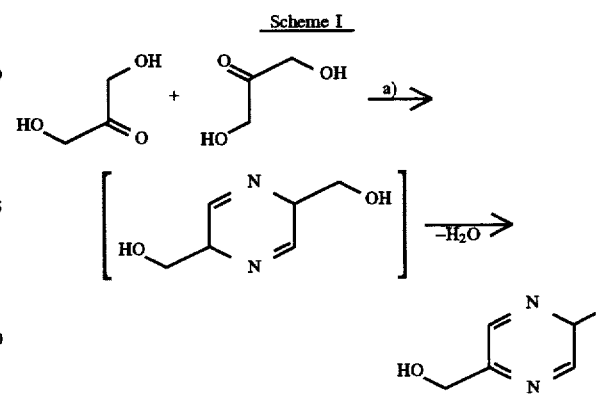

a) ammonium acetate, solvent

Furthermore, formation of 6-methyl-2-pyrazinemethanol, albeit in a lesser amount than the above-mentioned main product, can also be observed.

When 1,3-dihydroxy-2-propanone is reacted with an acyloin of formula (III), there will be further obtained substituted pyrazines such as those represented in the following scheme:

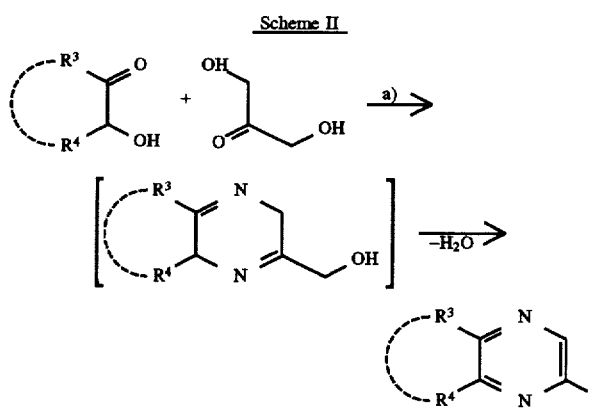

Scheme II a) ammonium acetate, solvent
$R^3$ and $R^4$ are defined as in formula (III)

Once again, when acyloin (III) possesses non-identical $R^3$ and $R^4$ substituents, there may also be observed formation of pyrazines which are isomers of that represented, and this probably as a result of the keto-enol tautomery of compound (I). Although such a tautomeric equilibrium is also possible for acyloin (III), we could not observe the formation of there-resulting pyrazines.

In both cases, the individual pyrazines forming the reaction product can be isolated by current methods, such as fractional distillation, chromatography, or other usual separation methods.

It is to be noted that the reaction conditions used are also favorable to the formation of symmetrical pyrazines, resulting from the reaction of acyloin (III) with the ammonium salt, in a manner analogous to that prior disclosed in the references previously cited.

Therefore, and depending on the nature of the reagents of formula (I), or of formulae (I) and (III), the reaction product can be a more or less complex mixture of asymmetrical pyrazines of formula (II), which mixture can also contain one or several asymmetrical pyrazines of formula (IV), which are then separated from the reaction mixture.

By "ammonium salt", it is meant here an ammonium salt derived from a carboxylic, sulfamic or mineral acid, preferably selected from the group consisting of ammonium acetate, ammonium citrate, ammonium tartrate, ammonium formate, ammonium oxalate, ammonium succinate, ammonium lactate, ammonium sulphamate, ammonium chloride, ammonium sulphate and ammonium phosphate (II) or (III). According to a preferred embodiment, ammonium acetate or formate is used.

The reaction takes place in an inert organic solvent. To this end, there can be used any solvent which is inert under the reaction conditions. Preferred solvents include methanol, ethanol, propanol, isopropanol, toluene, ethyl acetate or yet mixtures of two or more of these solvents. We also observed that the best yields in final product were obtained when an anhydrous solvent was used. According to a preferred embodiment, anhydrous ethanol will be used.

The starting products in the process of the invention are commercial products or products which can be readily prepared from commercially available chemicals. When they are available commercially in the form of aqueous solutions, the water is eliminated before their use. On the other hand, when it is desired to prepare pyrazines intended for use in natural flavors, starting products of appropriate quality, and the nature of which conforms to the legal norms in force, will be selected.

The relative proportions of the starting products (I) and (III) can vary in a fairly wide range of values, without much effect on the global reaction yield. However, the fact that each of the starting products can react with itself has an influence on the individual yields of each of the formed pyrazines, which yields can be modified by changing the molar ratio of compounds (I) and (III) (see tables presented further on).

Therefore, although these compounds can be used in a ratio compound (I)/compound (III) typically from 1:1 up to 1:3, we observed that when the acyloin was used in an amount above the stoichiometric ratio, say in a 2 to 1 excess, there was observed an increased yield in the asymmetrical pyrazine resulting from the reaction of compounds (I) and (III), to the detriment of the yield in the symmetric pyrazine resulting from the (III):(III) addition reaction. At the same time, there was also observed an increase in hydroxypyrazine coming from the (I): (I) self-addition. Thus, the relative ratio of compounds (I) and (III) can be chosen as a function of the price of the starting products and as a function of the nature of the final pyrazine that one desires to obtain in higher yield.

The reaction can be carried out at a wide range of temperatures, varying between room temperature and the solvent's reflux temperature. According to a preferred embodiment, this reaction will be carried out at the solvent's reflux temperature. On the other hand, whereas a solution of the ammonium salt can be added to the mixture of compounds (I), or (I) and (III), it was observed that better yields were obtained when the solution of acyloin (III) and dihydroxyketone (I), or only of the latter, in the selected solvent was slowly added to the ammonium salt, at the solvent's reflux temperature.

The invention will now be described in more detail by way of the following examples, wherein the temperatures are indicated in degrees centigrade and the abbreviations have the usual meaning in the art.

EMBODIMENTS OF THE INVENTION

EXAMPLE 1

Use of 1,3-dihydroxy-2-propanone as a reaction substrate

General method 1,3-Dihydroxy-2-propanone and, if applicable, the acyloin of formula (III), was dissolved in anhydrous ethanol by heating the mixture to reflux (80°).

The resulting solution was allowed to cool to room temperature and placed in a dropping funnel attached to a 500 ml three-necked flask containing solid ammonium acetate (or another ammonium salt). The flask was fitted with a water-cooled condenser and a stirrer and then heated to reflux (80°). The 1,3-dihydroxy-2-propanone solution was then added drop-by-drop over a 20 min period and the whole mixture kept at reflux for a further 2 to 3 h.

The mixture was allowed to cool to room temperature and the pH brought to 1 with HCl. Acetic acid and the neutral phase were extracted from the mixture with three volumes of $Et_2O$. The combined organic layers were washed again with 5 M HCl and the latter was added to the aqueous layer. The pH of the mixture was adjusted to 11 with NaOH pellets, while keeping the temperature at a low value by means of an ice bath. After extracting again with ether (3 times) and drying the organic extracts over anhydrous MgSO$_4$, the mixture was filtered and the solvent evaporated under vacuum.

The obtained basic fraction was distilled from residue in a bulb-to-bulb apparatus and the product obtained was analyzed by gas chromatography.

A. Preparation of 5(6)-methyl-2-pyrazinemethanol

Obtained by reacting 46 g (~0.5 mole) of 1,3-dihydroxy-2-propanone (origin: Merck, 99% pure), in 60 g of ethanol, with 57.8 g (0.75 mole) of solid ammonium acetate, according to the above-described process. The acidic/neutral fraction (10.18 g) was separated as described and the basic fraction (5.52 g) was distilled from residue at 75° and 8 Pa to provide 4.6 g of a pale yellow oil, the chromatographic analysis of which revealed a single peak (purity: 98.5%; total yield in pyrazine: 14.3%).

The GC-MS, $^1$H-NMR and $^{13}$C-NMR analysis of this product revealed that it consisted of a mixture of 5-methyl-2-pyrazinemethanol and 6-methyl-2-pyrazinemethanol (major isomer: minor isomer 3:2).

NMR($^1$H,360 MHz):

major isomer: 2.57(s,3H); 4.78(s,2H); 8.39(2,1H); 8.54(s, 1H) δ ppm minor isomer: 2.57(s,3H); 4.78(s,2H); 8.37(2,1H); 8.46 (s,1H) δ ppm

NMR ($^{13}$C):

major isomer: 152.7(s); 152.3(s); 143.3(d); 141.8(d); 62.9 (t); 21.1(q) δ ppm minor isomer: 154.8(s); 152.9(s); 142.9(d); 139.5(d); 63.0 (t); 21.3(q) δ ppm MS: 124(M$^+$,91); m/e: 123(59), 95(100), 66(19), 55(27), 42(32), 39(44)

B. Preparation of 2,3,5-trimethylpyrazine

Obtained according to the general method described, by reacting 1,3-dihydroxy-2-propanone (22.5 g, 0.25 mole) and acetoin (3-hydroxy-2-butanone; 29.7 g, 0.25 mole) in 40 ml of ethanol, with 57.8 g (0.75 mole) of solid ammonium acetate.

The basic fraction was distilled from residue at 60°–65° and 10×10$^2$ Pa to yield a pale yellow oil (13.91 g) and 5.05 g of residue.

Chromatographic analysis of this product showed that the distilled fraction contained 81% of 2,3,5-trimethylpyrazine (yield: 36.8%) and 17% of tetramethylpyrazine (yield: 13.9%), whereas the residue contained 5.8% of trimethylpyrazine, 13.9% of tetramethylpyrazine and 40.5% of 5(6)-methylpyrazinemethanol mixture (yield: 13.2%).

2,3,5-Trimethylpyrazine was separated from a distilled fraction obtained in identical manner but at a molar scale (63.0 g), by fractional distillation on a Fischer type column at 64×10$^2$ Pa. The following results were obtained:

| Fraction | Boiling point (°C.) | Weight (g) | 2,3,5-Trimethyl-pyrazine (%) |
|---|---|---|---|
| 1 | 55–66 | 2.30 | 0.3 |
| 2 | 66–65 | 5.66 | 5.1 |
| 3 | 65–69 | 1.38 | 5.2 |
| 4 | 69–87 | 2.33 | 45.3 |
| 5 | 87–88 | 16.96 | 98.9 |
| 6 | 85–87 | 8.04 | 99.2 |
| 7 | 87–88 | 11.99 | 97.2 |
| 8 | 88–88 | 1.07 | 65.8 |
| Residue | | 6.99 | |
| Total | | 56.72 | |

Fractions 5–7 were combined (total weight: 39.99 g), representing a yield of 32.8% in isolated product. The NMR spectrum of this product confirmed that it consisted of pure 2,3,5-trimethylpyrazine.

The following table indicates the obtained yield upon variation of the reaction conditions.

TABLE I

| Experiment | Acetoin (g) | 1,3-Di-hydroxy-2-propanone (g) | Solvent | Amount of solvent for acetoin (ml) | Ammonium acetate (g) | Solvent for ammonium acetate (ml) | Acetoin/dihydroxy-propanone molar ratio | Addition temperature (°C.) | Neutral/acidic fraction (g) | Raw pyrazinic fraction (g) |
|---|---|---|---|---|---|---|---|---|---|---|
| 1 | 29.7 | 45.0 | EtOH | 60.0 | 57.8 | 0.0 | 0.5 | 25.0 | 40.6 | 15.9 |
| 2 | 29.7 | 45.0 | EtOH | 70.0 | 57.8 | 30.0 | 0.5 | 80.0 | 12.8 | 26.7 |
| 3 | 29.7 | 22.5 | EtOH | 60.0 | 57.8 | 0.0 | 1.0 | 25.0 | 32.5 | 11.1 |
| 4* | 29.7 | 22.5 | Toluene | 60.0 | 57.8 | 0.0 | 1.0 | 80.0 | 9.8 | 8.9 |
| 5** | 29.7 | 22.5 | EtOH | 0.0 | 57.8 | 60.0 | 1.0 | 80.0 | 3.2 | 10.7 |
| 6 | 118.8 | 90.0 | EtOH | 200.0 | 115.6 | 40.0 | 1.0 | 80.0 | 24.6 | 78.4 |

| Experiment | Distilled pyrazinic fraction (g) | Residue (g) | Pyrazines (GC %) 2,3,5-Trimethylpyrazine | Tetra-methylpyrazine | 5(6)-Methyl-2-pyrazinemethanol | Total (%) | Yields (based on acetoin) 2,3,5-Trimethyl-pyrazine (%) | Tetramethyl-pyrazine (%) | 5(6)-Methyl-2-pyrazine-methanol (%) |
|---|---|---|---|---|---|---|---|---|---|
| 1 | 10.1 | 4.6 | 47.8 | 30.2 | 15.2 | 93.2 | 15.9 | 18.0 | 2.5 |
| 2 | 21.0 | 3.2 | 69.1 | 2.1 | 22.8 | 94.0 | 47.6 | 2.6 | 7.7 |
| 3 | fractionated | | 51.3 | 2.0 | 7.2 | 60.5 | — | — | — |
| 4* | non dist. | | 46.0 | 35.7 | 7.4 | 89.1 | — | — | — |
| 5** | non dist. | | 13.5 | 74.7 | 2.5 | 90.7 | — | — | — |
| 6 | 63.0 | 13.1 | 62.1 | 12.2 | 2.1 | 76.4 | 32.0 | 11.3 | 1.1 |

*Azeotropic distillation of the water and acetic acid
**Addition of the reagents inversed

EXAMPLE 2

Reaction of 1,3-dihydroxy-2-propanone with a variety of acyloins and ammonium acetate or formate 1,3-Dihydroxy-2-propanone was reacted with a series of acyloins and ammonium acetate or formate, following the general method described in Example 1. The obtained pyrazines are indicated in Table II. This table also includes the results of the reaction between acetoin and hydrated (+)-(S)-erythrulose (reaction 7), used instead of 1,3-dihydroxy-2-propanone.

TABLE II

| Reaction | Acyloin (A) | 1,3-Dihydroxy-2-propanone or other(B) | A:A Product | A:B Product | B:B Product |
|---|---|---|---|---|---|
| 1 | [structure] | [structure] | [structure] | [structure] | [structure] |
| 2 | [structure] | [structure] | [structure] or [structure] | [structure] (6,7:1) | [structure] |
| 3 | [structure] | [structure] | [structure] or [structure] | [structure] (1:5,1) | [structure] |
| 4 | [structure] | [structure] | [structure] | [structure] | [structure] |
| 5 | [structure] | [structure] | [structure] | [structure] | [structure] |
| 6 | [structure] | [structure] | — | [structure] | [structure] |

TABLE II-continued

| Reaction | Acyloin (A) | 1,3-Dihydroxy-2-propanone or other(B) | A:A Product | A:B Product | B:B Product |
|---|---|---|---|---|---|
| 7 | 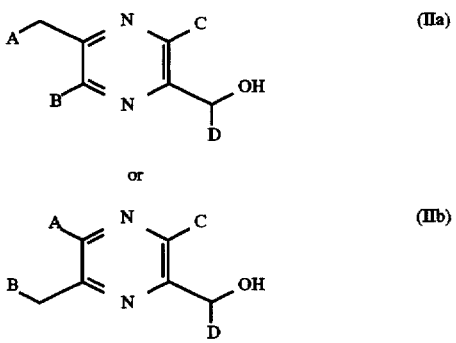 | | | | — |

The conditions of reactions 1 to 6 are summarized in Table III. The pyrazine percentages indicated relate to the content of the basic fraction, whether distilled or not. The identity of all the products obtained, cited in Table II or III, was confirmed by NMR ($^1$H and $^{13}$C) and GC-MS analysis.

TABLE III

| Reaction | Acyloin (mole) | 1,3-Dihydroxy-2-propanone (mole) | Ammonium acetate or formate (mole) | Product A:A (%) | A:B Product (%) | A:B Product (yield) |
|---|---|---|---|---|---|---|
| 1* | 0.25 | 0.25 | 0.75[a) | 20.3 | 72.0 | 22.6 |
| 2 | 0.02 | 0.019 | 0.049 | 17.2 | 86.4 | 42.1 |
| 3 | 0.02 | 0.019 | 0.049 | 12.2 | 86.4 | 41.2 |
| 4* | 0.017 | 0.017 | 0.043 | 18.0 | 59.0 | 25.0 |
| 5 | 0.022 | 0.022 | 0.055 | 18.7 | 79.2 | 48.9 |
| 6** | 0.05 | 0.05 | 0.125 | — | 88.6 | 3.2 |
| 7 | 0.021 | 0.021[b) | 0.052 | b) | b) | |

*Basic fraction not distilled
**Solvent used: ethanol/ethyl acetate 1:1
a) Ammonium formate
b) Hydrated (+)-(S)-erythrulose used instead of 1,3-dihydroxy-2-propanone; distillation and purification of the basic fraction provided a fraction containing essentially the A:A product (92%), a fraction containing essentially 3,5,6-trimethyl-6-pyrazinemethanol (66%) and a fraction containing essentially 2-(2-hydroxymethyl)-5,6-dimethylpyrazine (80.3%).

I claim:

1. A process for the preparation of a substituted pyrazine of formula (IIa)

(IIb)

wherein A=B=C=D=R$^1$=R$^2$, or wherein A=C=R$^1$, B=D=R$^2$, and R$^1$≠R$^2$, or A=D=R$^1$, B=C=R$^2$, and R$^1$≠R$^2$, symbols R$^1$ and R$^2$ representing each a hydrogen atom, a saturated or unsaturated, linear or branched, hydrocarbon radical having 1 to 6 carbon atoms or a —CH$_2$OH group; or alternatively of formula (IV)

wherein A'=R$^3$, B'=R$^4$ or vice versa and C'=R$^1$, D'=R$^2$, R$^1$ and R$^2$ being identical or different and having the abovementioned meaning and R$^3$ and R$^4$ being: a) identical or different and representing each: i) a saturated or unsaturated C$_1$ to C$_6$ hydrocarbon radical; or ii) a saturated or unsaturated cyclic radical, substituted or unsubstituted, having 5 or 6 carbon atoms in the ring; b) or being identical and representing a CH or CH$_2$ radical belonging to a common saturated or unsaturated ring, as indicated by the dotted line, having 5 or 6 carbon atoms, the process being characterized by the reaction, in an inert organic solvent, of a compound of formula

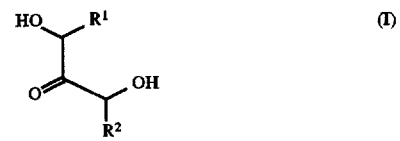

(I)

wherein R$^1$ and R$^2$ are identical or different and have the meaning indicated above, with an ammonium salt, or alternatively with an ammonium salt and an acyloin of formula

(II)

wherein R$^3$ and R$^4$ have the meaning indicated in formula (IV) and, if need be, by the separation of said pyrazine from the reaction product.

2. The process according to claim 1, characterized in that the acidic ammonium salt is selected from the group consisting of ammonium acetate, ammonium citrate, ammonium tartrate, ammonium formate, ammonium oxalate, ammonium succinate, ammonium lactate, ammonium sulphamate, ammonium chloride, ammonium sulphate and ammonium phosphate.

3. The process according to claim 2, characterized in that ammonium acetate or formate is used.

4. The process according to anyone of the preceding claims, characterized in that the solvent is methanol, ethanol, propanol, isopropanol, toluene, ethyl acetate, or a mixture of two or more of these solvents.

5. The process according to claim 4, characterized in that anhydrous ethanol is used as a solvent.

6. The process according to any one of claim, 1–3, or 5, characterized in that the reaction is carried out at a temperature between room temperature and the solvent's reflux temperature.

7. The process according to claim 6, characterized in that the reaction is carried out at the solvent's reflux temperature.

8. The process according to claim 1, characterized in that a solution of dihydroxyketone(I), or of dihydroxyketone(I) and acyloin(III), in ethanol is slowly added to the ammonium salt at the reflux temperature of ethanol.

9. The process according to claim 8, characterized in that the ammonium salt is ammonium acetate.

10. The process according to claim 4, characterized in that the reaction is carried out at a temperature between room temperature and the solvent's reflux temperature.

* * * * *